(12) United States Patent
Thodberg (10) Patent No.: US 7,848,893 B2
(45) Date of Patent: Dec. 7, 2010

(54) METHOD FOR SKELETAL MATURITY DETERMINATION

(76) Inventor: Hans Henrik Thodberg, Søllerødvej, DK-2840 Holte (DK)

( * ) Notice: Subject to any disclaimer, the term of this patent is extended or adjusted under 35 U.S.C. 154(b) by 296 days.

(21) Appl. No.: 11/921,153

(22) PCT Filed: May 29, 2006

(86) PCT No.: PCT/DK2006/000293
§ 371 (c)(1),
(2), (4) Date: Nov. 28, 2007

(87) PCT Pub. No.: WO2006/128461
PCT Pub. Date: Dec. 7, 2006

(65) Prior Publication Data
US 2009/0105958 A1    Apr. 23, 2009

(30) Foreign Application Priority Data
Jun. 2, 2005    (DK) .................. PA 2005 00801

(51) Int. Cl.
*G01N 33/48*    (2006.01)
*G01N 23/223*    (2006.01)
*G06K 9/00*    (2006.01)
*G01B 15/02*    (2006.01)
*G01B 15/04*    (2006.01)

(52) U.S. Cl. .................. 702/19; 378/50; 378/51; 378/54; 382/132

(58) Field of Classification Search .................. 702/19; 382/132; 378/54, 50, 51
See application file for complete search history.

(56) References Cited

U.S. PATENT DOCUMENTS

| 6,763,257 B1 | 7/2004 | Rosholm et al. |
| 2004/0101186 A1* | 5/2004 | Tong et al. .................. 382/132 |

FOREIGN PATENT DOCUMENTS

| EP | 0 626 656 A2 | 11/1994 |
| EP | 1 293 925 A1 | 3/2003 |

OTHER PUBLICATIONS

Niemeier M et al., "Assessing the skeletal age from a hand radiograph: automating the Tanner-Whitehouse method" vol. 5032, 2003, pp. 1197-1205.
Tanner J M et al., "Automatic Bone Age Measurement Using Computerized Image Analysis" vol. 7, No. 2, Apr. 1994, pp. 141-145.

(Continued)

*Primary Examiner*—Hal D Wachsman
*Assistant Examiner*—Janet L Suglo
(74) *Attorney, Agent, or Firm*—Birch, Stewart, Kolasch & Birch, LLP (57) ABSTRACT

The invention is a method for estimating a skeletal maturity value of a human from a radiograph of one or more bones in the hand. The borders of the bones are represented by shape points, which are subjected to principal component analysis (PCA). Image intensities are sampled at points located relative to the shape point, and also compressed with PCA. From the features a skeletal maturity value is determined.

11 Claims, 4 Drawing Sheets

OTHER PUBLICATIONS

Thodberg H H: "Hands-on experience with active appearance models" vol. 4684, 2002, pp. 495-506.

Martin-Fernandez M A et al., "Automatic bone age assessment: a registration approach" vol. 5032, 2003, pp. 1765-1776.

Kauffman J A et al., "Segmentation of hand radiographs by using multi-level connected active appearance models" vol. 5747, No. 1, May 2005, pp. 1571-1581.

Bovik, Alan Conrad et al., "Multichannel Texture Analysis Using Localized Spatial Filters", IEEE Transactions on Pattern Analysis and Machine Intelligence, vol. 12, No. 1, pp. 55-73, Jan. 1990.

Cootes, T.F., et al., "Statistical Models of Appearance for Computer Vision", Technical Report, Wolfson Image Analysis Unit, Imaging Science and Biomedical Engineering, pp. 1-124, Mar. 8, 2004, University of Manchester.

Dryden, I.L. et al., "Preliminaries: Planar Procrustes Analysis", Statistical Shape Analysis, pp. 39-51 and one additional page, 1998.

Greulich, William Walter et al., "Radiographic Atlas of Skeletal Development of the Hand and Wrist", 2nd Edition, pp. vii-xvi, 1-61, 185-196, 1959, Stanford University Press, Stanford, California.

Hilger, Klaus B. et al., "Markov Random Field Restoration of Point Correspondences for Active Shape Modelling", Proceedings of SPIE, Medical Imaging, vol. 5370, pp. 1862-1869, 2004.

Kotcheff, Aaron C.W. et al., "Automatic Construction of Eigenshape Models by Direct Optimization", Medical Image Analysis, vol. 2, No. 4, pp. 303-314, 1998.

Larsen, Rasmus, "Shape Modelling Using Maximum Autocorrelation Factors", six pages, Proceedings of SCIA, 2001.

Niemeijer, M., "Automating Skeletal Age Assessment", Master's Thesis, pp. 1-73, Jul. 19, 2002, Universiteit Utrecht.

Tanner, J.M. et al., "Assessment of Skeletal Maturity and Prediction of Adult Height (TW2 Method)", 2nd Edition, pp. v-vii, 1-14, 41-45, 54, 55, 78 & 79, Sep. 1975, Academic Press, London.

Thodberg, H.H. et al., "Application of the Active Model in a Commercial Medical Device for Bone Densitometry", Image and Vision Computing, vol. 21, pp. 1155-1161, 2003, Elsevier B.V.

Üzümcü, M. et al., "ICA vs. PCA Active Appearance Models: Application to Cardiac MR Segmentation", pp. 451-458, Medical Image Computer-Assisted Intervention—MICCAI 2003, 2003, Springer-Verlag Berlin Heidelberg.

* cited by examiner

METHOD FOR SKELETAL MATURITY DETERMINATION

BACKGROUND OF THE INVENTION

1. Field of the Invention

Figure 1:
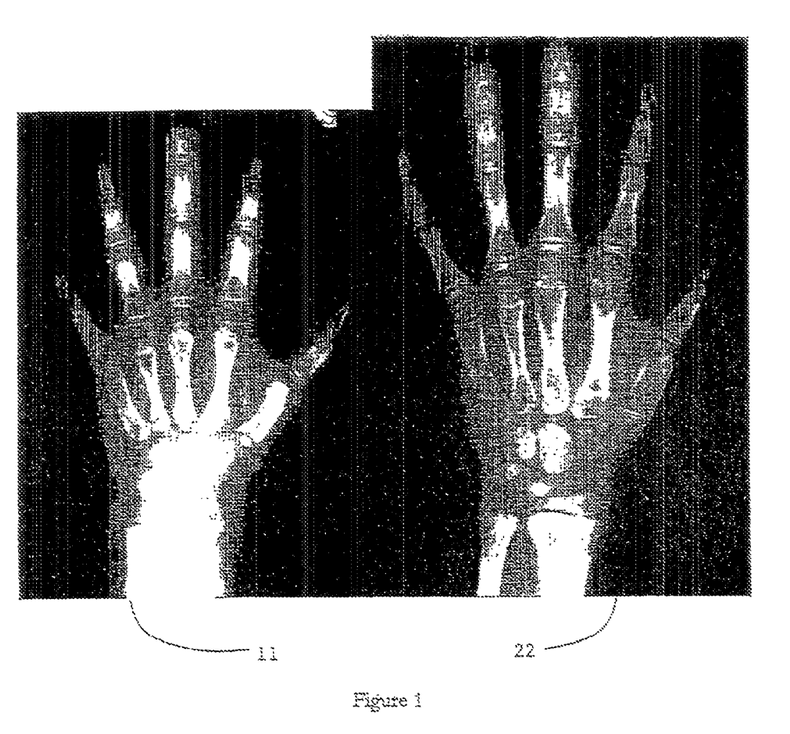
FIG. 1 shows had radiographs of a two-year-old child and a five-year-old child.

The bones of the human body undergo a dramatic change of shape and structure as the body matures until the age of approx 18 years. This is illustrated in FIG. 1, showing a 2-year old child on the left (11) and a 5-year old child on the right (22). This maturation process does not proceed exactly according to the chronological age of the person; it is typical that some children are up to two years ahead or behind.

Figure 2:
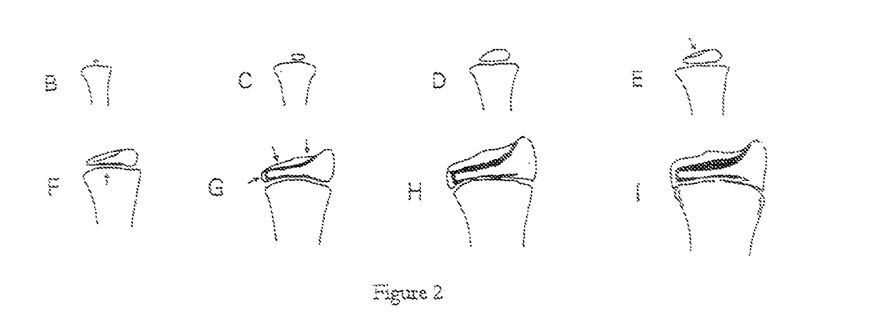
FIG. 2 illustrates stages of maturation of the Tanner-Whitehouse method.

In medicine it is important to determine the development stage of the skeleton e.g. as an element in the diagnosis of various growth disorders, e.g. growth hormone deficiency, and hand radiographs as shown in FIG. 1 have become the standard means of investigation. The most reliable radiological method used today is the Tanner-Whitehouse (TW) method [1]. In its most common version it utilises 13 bone regions, which are each assigned a stage of maturation manually by visual inspection. There are 8 or 9 stages for each bone described in terms of stylised images and verbal description of radiological features. The TW stages of the radius are shown in FIG. 2, and the children in FIG. 1 thus seem to have radius of stage D (or E) and F respectively. The TW method has defined sex-dependent scores to be attributed to each stage, and the scores thus assigned to the 13 bones are added to form the summed maturity score (SMS). The TW method developers have collected population data of the SMS of normal children, from where they have computed the SMS centiles versus chronological age. This allows the SMS observed for a child under medical examination to be compared with a normal population. Most often the observed SMS is translated into a bone age defined as the age, at which the observed SMS is reached in half of the population.

Another popular scheme is the Greulich-Pyle (GP) method, where the child's X-ray is matched to one of the images in an atlas with images covering all bone ages [12].

There are a number of problems with the TW method: Firstly it is time-consuming. Secondly it is tedious. And thirdly it has a considerable inter-observer variation; the difference between two observers is typically 0.4-0.6 years (SD) or even larger in some instances. Therefore a lot of effort has been invested in automating the procedure using computers, starting in 1989 and culminating in 1992-94, where it was realised that it is technically very difficult, see Niemeijer [2] for a review. The development activity has continued, but still today, no satisfactory automatic system has been made.

2. Description of the Related Art

Thus there is a vast body of prior art in this area and to clarify the new and inventive steps of the invention, the prior art is summarised in the following.

The methods investigated so far, as well as the new invention herein, involve two distinct steps of processing: Bone localisation (sometimes denoted segmentation or reconstruction) and bone interpretation.

A) Bone localisation: The purpose of this step is to identify the bone regions that TW specifies should be rated. Various approaches have been taken in this step:
  a. Manual placement of the region of interest (ROI), by translating, rotating and resizing the image to fit a fixed template
  b. Standard pattern recognition methods based on thresholding etc.
  c. Snakes
  d. Active shape model (ASM)

B) Bone interpretation: The purpose of this step is to derive the maturity from the bone ROI. Again several methods have been applied
  a. Fourier coefficients
  b. Correlation between the image ROI and a template for each stage
  c. Width of epiphysis relative to metaphysis
  d. Shape parameters (derived from the ASM of the bone localisation)
  e. Semantics/rule-based post-processing of features closely emulating the descriptions of TW stages The typical idea has been to emulate as well as possible the classification into TW-stages, with the added feature of smoothly interpolations between stages.

THE INVENTION

The present invention deals with step B, the interpretation of the already localised bones. The first part of the automation in the proposed method can be accomplished by ASM, or by active appearance models (AAM) or extensions of AAM and combinations thereof [4]. The core of the invention, corresponding to claim 1, is the interpretation of the localised bone. The method is characterised by the following three steps:

1) Extracting parameters indicative of the shape of the bone border. This is accomplishing by defining shape points on the border. The preferred embodiment is to subject these shape point coordinates to a principal component analysis (PCA) and use the first principal components as the extracted shape parameters.
2) Extracting parameters indicative of the image intensities sampled in the bone region at 10 or more locations defined relative to the shape points. The parameters are preferably derived from a PCA of the intensity vector after normalising this vector to standard variance.
3) A prediction formula with the parameters obtained in step 1 and 2 as input and maturity value as output.

Comment on 1): The described PCA model is the kind of shape model underlying ASM, AAM and variations thereof. It is constructed by defining shape points along the border of a number of examples of the bone; this can be done manually or automatically. The process then applies a rigid transformation to each example to bring it as close as possible to the mean shape; a preferred embodiment for doing this is the Procrustes analysis [13]. Then the process concatenates the x and y coordinates to a single vector and performs PCA on this, and one or more principal component scores are then used as abstract shape descriptors, corresponding to the dominant modes of the biological variation. The shape points, which form the input to the PCA, are preferably chosen to be corresponding, i.e. placed at analogous anatomical location throughout the data set. This can be obtained in several manners, the preferred embodiment is the one described by Kotcheff and Tailor [3], in which the points are defined by an optimality criterion in terms of compactness of the PCA.

Comment on 2): This representation of the image information is the kind used in AAM for localisation, but here it is used for interpretation. Thus, as in AAM, one can implement the sampling by computing a triangulation [4] of the image region from the shape points (see FIGS. 3 and 4, more details are given below). In one embodiment this can be a Delaunay triangulation. In the mean shape the process defines sampling points relative to their coordinates in this triangulation. This method can now be applied to a new example. In this example, the shape points occur deformed relative to the mean, but the sampling points can be computed from the deformed triangulation. In other words the observed image is warped to the mean shape before sampling the intensities, and alternative methods for warping can be used instead with the same effect, for instance thin-plate-splines.

In 1) and 2) the PCA can be replaced by other transformation leading to a compression of the high-dimensional data into a small number of components describing the relevant variation. Other methods of this family are independent component analysis, MAF, PLS (see [7, 8]). When PCA is mentioned in this application it is understood to also encompass these transformations.

Comment on 3) the maturity value can be either the TW stage, the scores corresponding to the stage, or a bone age. The formula can be dedicated to a small range of maturation, e.g. the separation of two stages, or it can cover a larger interval of ages. The model can be linear, e.g. linear regression of logistic regression, or non-linear e.g. using a backpropagation neural network.

The topology of the bones change over the age span from 0 to 18 years, and the process therefore use one model for the age span where the epiphysis is separated and another model for the age range where it is fused. This allows the shape point definition to be different for the different age spans. The two sexes can be combined in one model, for instance a model of proximal phalanx 3 (PP3) with separate epiphysis can be made from boys aged 7-13 years and girls aged 6-12 years. The shape and intensity PCA then describe all the dominant variation in data from this age range. The prediction model may or may not include the known gender of the subject, depending on whether maturity or age is modelled.

SUMMARY OF THE INVENTION

Following the description above, the effect and advantages of the invention is discussed in this section.

Firstly, several authors have used ASM for the localisation of the bones. Using AAM has the advantage of more reliable reconstruction of the bones. Other methods can also achieve good localisation.

Secondly the use of the entire shape information in terms of a low-dimensional representation has the advantage that the entire shape information is well-described using only a few variable. Subtle features of the shape, which are not easily described in words, are also included in this manner.

Figure 3:
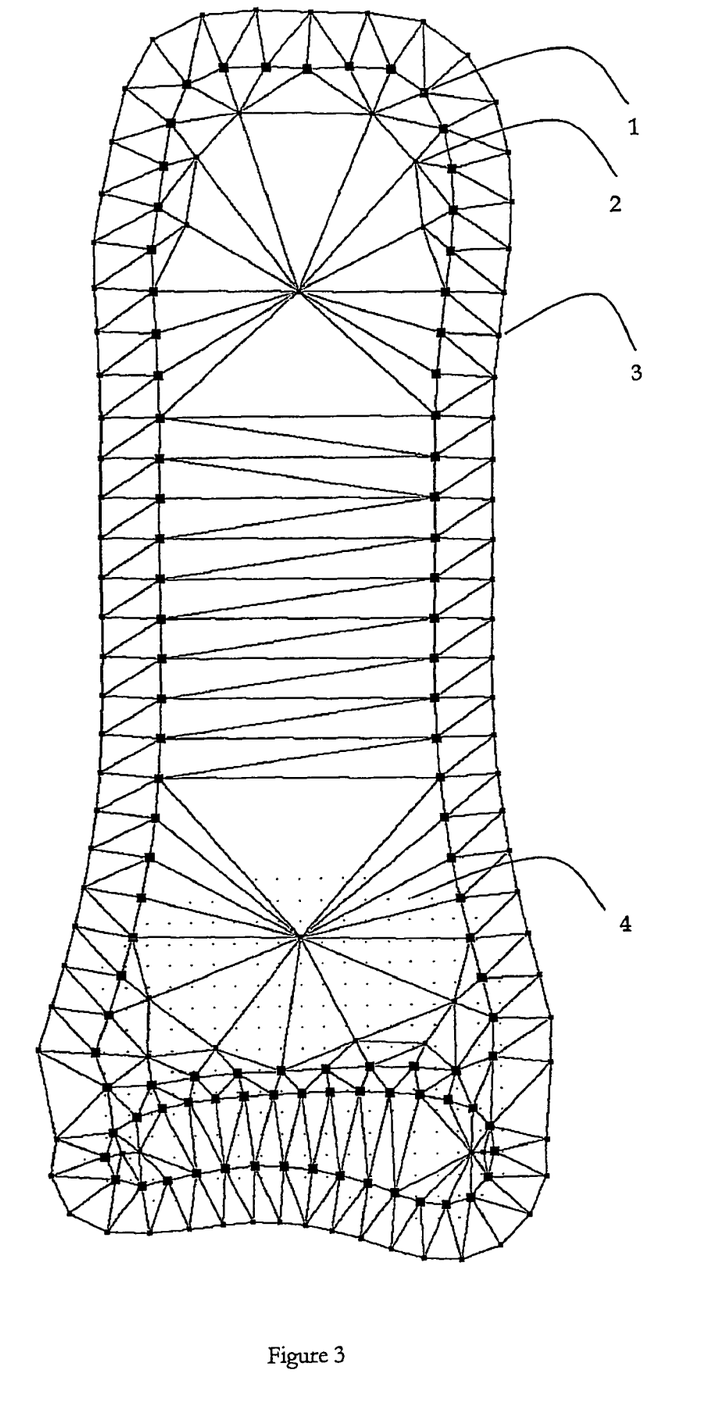
FIGS. 3 and 4 illustrate a computer triangulation of an image of a bone region.

Thirdly, the image intensities are sampled at points which are placed relative to the localised bone boundary, e.g. using the triangulation method of FIG. 3. This is more powerful than sampling according to a rigid template matched to the bone, as has been done by many authors, e.g. [2]. With a rigid template, a given sampling point will not be at a location corresponding to the same anatomical location across many examples. For instance a sampling point which on the template is just outside the bone can be occurring inside the bone on a specific example. This means that the sampled intensities reflect a mixture of shape and intensity variation and therefore are less specific to the intensities. This in turn prevents the image intensity vector to be compressed to a low-dimensional representation. Also when a sampled value is not at the same anatomical location the discriminative value of the information deteriorates.

Fourthly, the use of both shape and image features in the prediction formula has the advantage that the prediction can be based on an almost complete information on both shape and intensities. Because the shape information has been taken out of the intensity features, the two complement each other in the best way. As part of this step of the invention one can combine the shape and intensity scores into a common PCA model, analogous to what is done in AAM, obtaining what is denoted the c-scores or appearance scores in this framework [4].

The method as a whole deviates qualitatively from previous approached by taking a holistic, sub-symbolic, connectionist approach to maturity determination, as is explained in the following: The TW stage description is rule-based and many previous attempts have focussed on using features which have a verbal description to mimic the TW-description. On the contrary, the present invention insists on using an almost complete representation of the shape and intensity information of the bone region as an integral block forming the input to a prediction model. The method is characterised by separating the shape description in one set of parameters and then defining the image information taking the deformable shape into account, i.e. the bone is deformed to the mean bone before interpreting the intensity values. The method is also characterised by using both shape and intensity values as inputs to the model.

BRIEF DESCRIPTION OF THE DRAWINGS

The present invention will become more fully understood from the detailed description given hereinbelow and the accompanying drawings which are given by way of illustration only, and thus are not limitative of the present invention, and wherein.

DETAILED DESCRIPTION OF THE PREFERRED EMBODIMENTS

Figure 5:
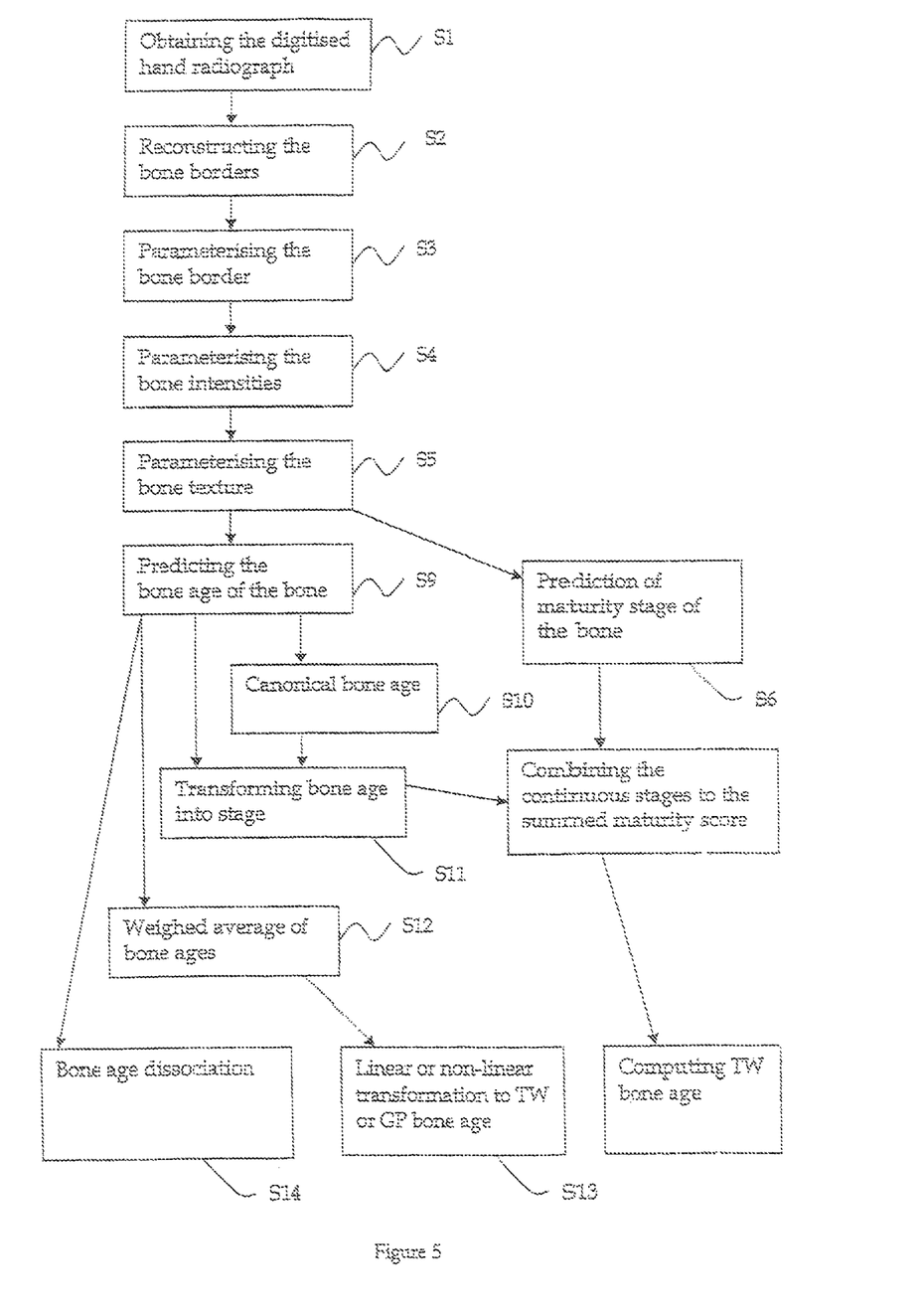
FIG. 5 illustrates a flow diagram of an embodiment of a method for estimating the skeletal maturity value of a human body.

The steps of most of the embodiments of the invention are shown graphically in FIG. 5, which contains a number of steps enumerated S1-S14, to which the following text refers.

A preferred embodiment (claim 2) is using PCA or similar methods to compress the high-dimensional shape and image data into a lower-dimensional representation (in S3 and S4 respectively). By similar methods is meant other methods which also implements unsupervised learning of which PCA is the most common example. Here the spatial correlation of the data causes the method to extract salient features of data as learned from a training set. The advantage is that PCA learns important features of maturation by unsupervised learning. Thus the first mode of variation of the shape model of 6-13 years old PP3 turns out to be dominated by the variation of the epiphysis width relative to the metaphysis width. This feature is not entered in the method by hand as prescribed by the TW rating system, but is derived from the data themselves by means of the shape PCA. In analogy with this, other shape features are extracted automatically. Similarly, image features describing characteristic changes of density distribution with maturation are deduced by the PCA. Therefore the proposed method derives more information from the images than prescribed by the verbal TW stage descriptions, and this is furthermore done automatically, and this renders the models more powerful. Thus the method provides a robust and more exhaustive description of the maturation as it appears in projection radiographs.

A preferred embodiment of the invention, as reflected in claim 3, is extracting in addition a set of image texture features in the bone ROI (FIG. 5, S5). "Texture" denotes patterns of pixel intensities defined locally, the patterns characterised by being sensitive to a wavelength range and direction interval. The texture is preferably Gabor filter energies, where the orientations of the filters are defined relative to the orientation of the bone as localised by the earlier steps of the algorithm. The texture energies are sampled at least 10 points whose location are defined relative to the shape points and covering the bone ROI or part thereof and normalised to the contrast of image intensities in the bone region and subjected to a PCA derived from a training set. The texture PCA scores are used as additional inputs to the prediction model. The advantage is that this process is indicative of the closing of the growth zone and appearance of internal edges without specifying them explicitly. This is particularly important for the older children.

Most authors have modelled the maturity stage directly. However, as an alternative (claim 4), one can model instead the age, preferably the chronological age (S9 in FIG. 5). This can be done by a model of the form $$\text{Age} = \text{bias} + \text{slope} * (a1*f1 + a2*f2 + \ldots + an*fn)$$

where $f1, \ldots, fn$ are the features from the bone, i.e. the PCA components of shape, intensity and texture, and the model parameters $a1, \ldots, an$ are the same for both sexes, while the model parameters bias and slope are sex-dependent.

In this way the process predicts the chronological age for each bone as well as it can from the image. However, this can only yield the apparent age, and this predicted chronological age is therefore defined as (interpreted as) the bone age of the bone.

A preferred embodiment (claim 5) is to form a weighted average of these first estimates of bone ages and use this as target variable for a second round of regression, where the features of each bone are used to predict the average bone age of the hand (S10 in FIG. 5). The weights in the weighted average can be equal, or unequal emphasising some bones more than others, and possibly excluding the bone itself. The advantage of this way of modelling is that it corresponds better to the nature of maturation: If maturation is delayed it will most often be delayed in all the bones with approximately the same amount. The effect of this embodiment is that the maturity determinations from each bone determine a bone age, which is the consensus of the all the bones appearances wrt maturity. The bone age of this embodiment is denoted the canonical bone age because it is reminiscent to the result which would be obtained by a canonical correlation analysis of the features of the individual bones. The advantage is that the training signal is more reliable and the model is therefore a better description of the true maturity.

The predicted age can be viewed as a maturity value, and this can be transformed by a non-linear monotonic function (claim 6) to be indicative of the TW stage on a training set, so that the rounded values agrees best with the TW stages (S11 in FIG. 5). In this translation into stages, boys and girls can be pooled by resetting slope to 1 and bias to 0 in the formula above. The advantage of this claim is that the translation to stage is done as a relatively simple post-processing of the predicted age. Since it is simple it requires a smaller data set to estimate this mapping.

The bone ages of the individual bones can also be used in a weighted average to form an overall estimate of bone age (claim 7) (S12 in FIG. 5). The weights can be dependent on age or bone age, reflecting that some bones play a larger role in some age intervals. For instance the radius typically reaches full maturity later than the phalanges. The advantages of this method of estimating bone age is that it is more transparent how the bone age is constructed, and it allows for omitting some bones in the estimate, e.g. if the bone or its image is damaged.

The overall bone age can be linearly or non-linearly transformed to correspond to the TW bone age or GP bone age based on a training set (claim 8) (S13 in FIG. 5). This transformation is needed because the dataset used to estimate the bone ages according to claim 4 and 5 is in general a different population than the one used to define the standard TW SMS centiles and hence the bone age. The advantage of this embodiment is that it is a simple manner to adjust the bone age of claim 7 to many different populations.

The dispersion of the bone ages of the set of bones is itself an informative concept, called the maturity dissociation (S14 in FIG. 5). It can be expressed as standard deviation of the bone ages, or as separate bone age averages over various parts of the hand, the radius/ulna part, the metacarpals, the phalanges, and one can make statements such as "the bone age of the phalanges is 1.5 years ahead of radius/ulna" etc. The advantage of this is that it gives more detailed information which can be used as part of the diagnosis by the medical expert.

Instead of predicting the chronological age as outlined above, another embodiment (S6 in FIG. 5) is using the features of the PCA to predict the maturity stage, based on a training set. Most classifiers are probabilistic in nature, so they provide probabilities of the stages, and this can used to interpolating the stage output to a continuous stages, for instance for the stages A, . . . , I one gets a continuous stage in the range 1-9 or 0.5 to 9.5, where 8.5-9 is the lower half of stage 1 and 9-9.5 is the upper half of stage I. The advantage of this embodiment is that it brings the analysis onto the road of conventional TW-rating and the scores can be associated to the stages, but interpolating, forming the summed maturity score, and from the reference data base forming the TW bone age.

From FIG. 5 it is clear that there are two main roads of the invention, the one predicting age for each bone and the one predicting the continuous stage directly.

The method can in a preferred embodiment be performed on a suitably programmed computer, or a system of several computers, which can be at separate physical locations and connected by a network, e.g. the Internet. The method can be embodied as a computer program, or a computer-readable medium. The method can be implemented as an Internet-service, where the user accesses the method in a web-browser, or as a component in a larger data-processing system.

In the following are given some details to describe exactly how to implement the steps mentioned so far.

The input to the method (FIG. 5, S1) is a digital image, for instance in the form of a TIFF file with a number indicating the intensity at every pixel. The image can be obtained from a radiographic film, which has been digitised using an optical scanner, or it can be obtained from a CR image recording it on a phosphor plate which is read off and digitised by the CR equipment, or by using a direct digital radiography detector outputting the intensities directly from the electronics. The image can also be from DEXA scanner of good spatial resolution and can then either be a mono-energetic image or a subtracted image. Associated with the image is also the spatial resolution in mm per pixels. Also the sex of the child has to be known to derive the bone age.

The identification of the bone borders (FIG. 5, S2) can be performed with active appearance models (AAM). In the first step the process searches simultaneously for 3 or 4 of the metacarpals because they form a pattern, which is simple to search for exhaustively at all locations and in all orientations, see [12] for details. The process searches both for left and right hands and the best search-result determines the interpretation. Subsequently the process locates the remaining bones by predicting a start search location based on the bones found so far. Such a complete framework for AAM reconstruction of bones in the adult hand was reported in reference [5]. In the present method the age is unknown and every time a bone is searched the process can apply several models corresponding to different maturity stages. For instance the process can use three models covering the age ranges 2-6 years, 6-13 years and 13-18 years, and the model that fits best is the selected reconstruction. In some of the younger models, the epiphysis is separated form the metaphysis.

Once the process has reconstructed the border, it extracts the shape points to represent the bone border (FIG. 5, S3). If the reconstruction model is AAM or ASM, this already provides shape points from the underlying PCA shape model. Otherwise the process can fit the border to a PCA-based shape model, i.e. parameterise the border as the mean shape transformed to a given pose (using a translation vector, a rotation angle and scaling factor, see [13]), and determine a deformation in terms of the shape parameters. ASM can be used to implement this as demonstrated in [10].

Figure 4:
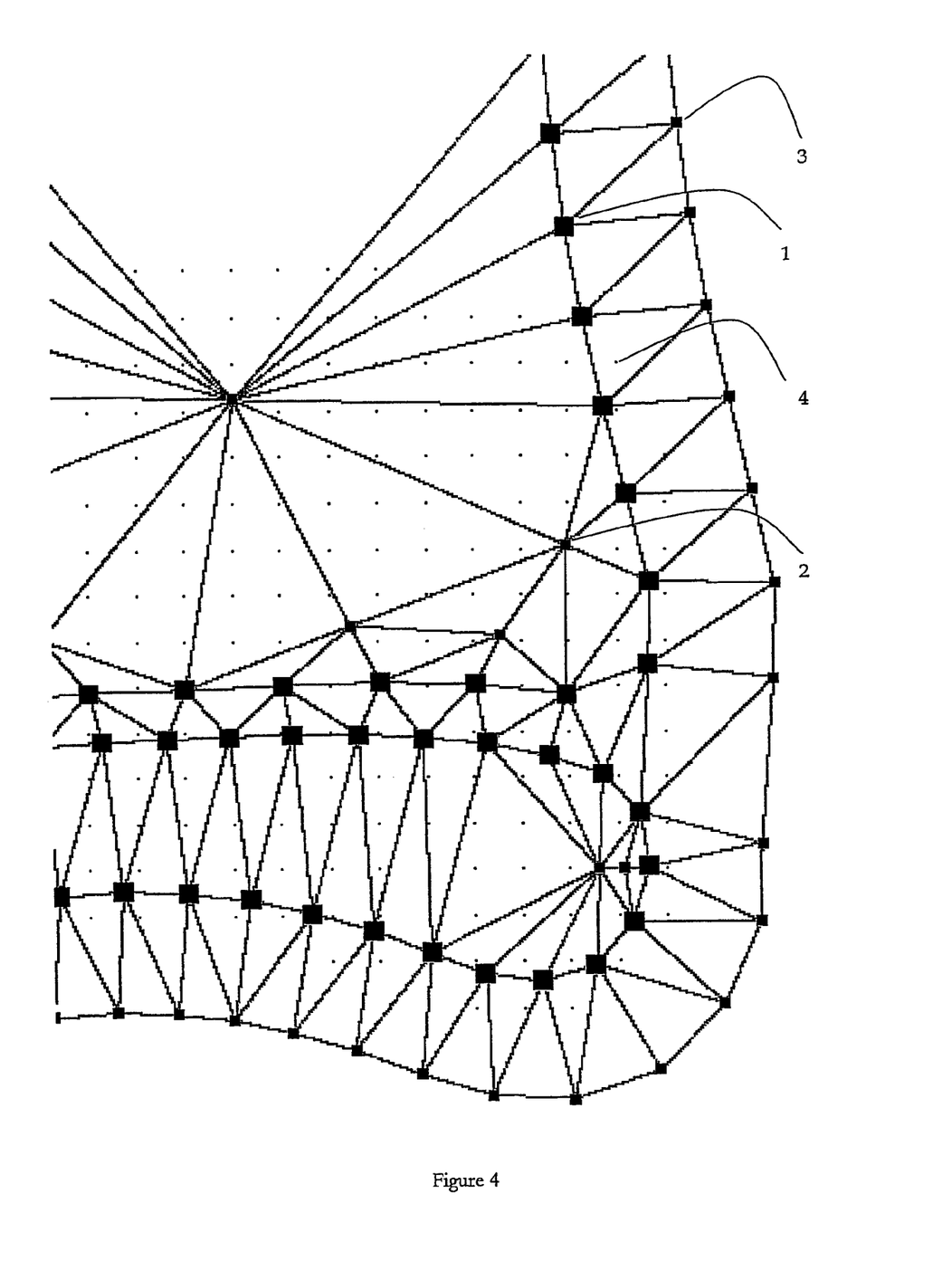

The extraction of a vector of sampled image intensities (FIG. 5, S4) is illustrated in FIGS. 3 and 4, which show the mean shape points in large squares (1), defined at the border of the bone. Auxiliary points can be defined away from the bone border, shown with smaller squares in FIGS. 3 and 4. In the interior (2), these points can be defined as interpolations between border points. At the exterior (3), each point can be defined relative to one of the border points at a certain angle and distance from this. The angle is defined relative to the axis of the bone and the distance is computed relative to the size of the bone.

The border and auxiliary points define the corners of the triangles; the auxiliary points ensure that the triangles span also a margin of the bone and avoids occurrence of triangles with very small angles.

Inside the triangulated area of the mean shape the process places sampling points for instance in a regular grid, as shown with the smallest points (4) in FIGS. 3 and 4. As exemplified in the embodiment in FIG. 4, which is a detailed view of part of FIG. 3, only part of the triangulated area can be used for sampling since the most important changes of the density are known to be in this part of the bone where growth occurs.

The process can in one embodiment also form texture features by defining a texture vector in each location of the image (FIG. 5, S5). Each element of the texture vector can reflect a certain wavelength and direction. The standard choice is the Gabor filters [9], but most other texture measures would give the same effect. A wavelength of 1 or 2 mm is appropriate to catch the signal of the border between the epiphysis and the metaphysis and its fusion.

Four to six directions are appropriate. In the simplest scheme, four directions and a single wavelength is used. This means that the image is filtered with four Gabor filters, each comprising a real and an imaginary part. The real and imaginary outputs are squared and added to form four energies per location. The square root can be taken to compress the dynamic range. The textures can be normalised with some number indicative of the image contrast derived from the same image, e.g. the standard deviation of the intensities in the bone region, leading to the final four bands of the texture image.

In an embodiment, the process samples four texture band images at the sampling points e.g. as those in FIG. 3 or 4, and the vector of samplings is subjected to a PCA defined previously on a training set.

REFERENCES

[1] J. M. Tanner, R. H. Whitehouse, N. Cameron, W. A. Marshall, M. J. R. Healy, and H. Goldstein: Assessment of skeletal maturity and prediction of adult height (TW2 method). Academic Press, London, 2nd edition, 1975.

[2] M. Niemeijer: Automating skeletal age assessment, Master's thesis, Utrecht University (2002).

[3] M. Kotcheff and C. J. Taylor: Automatic construction of eigenshape models by direct optimisation, Med. Image Anal., vol. 2 (1998) 303-314.

[4] T. F. Cootes and C. J. Taylor: Statistical models of appearance for computer vision. Technical report, Wolfson Image Analysis Unit, Imaging Science and Biomedical Engineering, University of Manchester, 2001.

[5] H. H. Thodberg: Hands-on Experience with Active Appearance Models, Medical Imaging 2002: Image Proc., Eds. Sonka & Fitzpatrick, Proc. SPIE Vol. 4684, 495-506 (2002).

[6] DXR-BMD U.S. Pat. No. 6,763,257 B1, by Rosholm and Thodberg. (This patent contains a lot of references and general discussion which serves as background for the present application).

[7] R. Larsen: Shape Modelling using maximum autocorrelation factors in Proceedings of SCIA '01, Bergen, (2001) p 98-103.

[8] M. Uzumcu, A. F. Frangi, J. H. C. Reiber, B. P. F. Lelieveldt (2003): ICA vs. PCA Active Appearance Models: Application to Cardiac MR Segmentation. In Medical Image Computing and Computer-Assisted Intervention—MICCAI'03, R. E. Ellis, T. M. Peters (Eds). Lecture Notes in Computer Science, vol. 2878, Springer Verlag, Berlin, Germany, pp. 451-8.

[9] A. Bovik, M. Clark, and W. Geisler. Multichannel texture analysis using localized spatial filters. IEEE Transactions on Pattern Analysis and Machine Intelligence, 12(1): 55-73 (1990).

[10] K. B. Hilger, R. R. Paulsen, R. Larsen, Markov Random Field Restoration of Point Correspondences for Active Shape Modelling, SPIE—Medical Imaging 2004.

[11] H. H. Thodberg and A. Rosholm, Application of the active shape model in a commercial medical device for bone densitometry. Image and Vision Computing 21, pp 1155-1161 (2003).

[12] W. W. Greulich and S. I. Pyle, Radiographic Atlas of Skeletal Development of Hand and Wrist, 2. ed., Stanford Univ. Press (1959).

[13] I. L. Dryden and K. V. Mardia, Statistical Shape Analysis, Wiley (1998).

What is claimed is:

1. A method to estimate the skeletal maturity value of a human, the method comprising:
   a. obtaining a digital radiograph of at least one bone of the human hand;
   b. determining a border of the bone and determining a set of at least 15 points on the border called shape points, each point representing a specific anatomical location on that the bone;
   c. determining a lower-dimensional representation of the shape points in terms of shape parameters derived from a transformation of the shape point coordinates;

d. sampling image intensities in a bone region or a part thereof, at sampling points defined relative to the shape points, followed by a transformation into a lower-dimensional representation yielding intensity parameters; and e. determining a skeletal maturity value from the determined representation of the border and the image intensities, the maturity being expressed as bone age, maturity stage, fractional stage or scores, wherein the steps a-e are performed by at least one computer.

2. The method according to claim 1, wherein the transformations used to form lower-dimensional representation of shape and intensity is defined as one or more of the principal components of a principal component analysis (PCA), applied to a training set of bone examples.

3. The method according to claim 1, wherein additional image features are included, by sampling of image texture values at points defined relative to the shape points, optionally normalising these texture values using a parameter derived from the same bone image, transforming these texture values to a lower dimensional representation to form one or more texture parameters, and using these texture parameters as additional input to the determination of the maturity value.

4. The method according to claim 1, wherein the maturity value is determined by a prediction formula, estimated on a training set of images of children, predicting the chronological ages of the children, and a prediction of the chronological age being denoted the bone age of the bone.

5. The method according to claim 4, wherein the said bone ages for several bones determined in that step are combined in the form of a weighted average and used as target in a second prediction formula that predicts the weighted average from each bone's parameters, and a predicted value of the weighted average is denoted the bone age of the bone.

6. The method according to claim 4 where the bone ages for each of the bones are transformed with a monotonous function, the result being denoted the continuous TW maturity stage.

7. The method according to claim 4, wherein the bone ages determined for each bone are used in a weighted average to form the overall bone age.

8. The method according to claim 7, wherein the overall bone age is transformed to a bone age indicative of TW-bone age or GP bone age.

9. The method according to claim 1, wherein the maturity value is a direct estimate of the TW stage of the bone, predicted as a continuous TW-stage.

10. A non-transitory computer readable medium containing a computer program comprising computer-executable instructions for performing the steps of the method of claim 1.

11. A computer programmed with computer-executable instructions stored in a non-transitory computer readable medium to perform the steps of the method of claim 1.

* * * * *